United States Patent [19]

Salamone et al.

[11] Patent Number: 4,987,893
[45] Date of Patent: Jan. 29, 1991

[54] CONFORMABLE BANDAGE AND COATING MATERIAL

[75] Inventors: Ann B. Salamone; Joseph C. Salamone, both of Boca Raton, Fla.; Alfred P. Olson, Center Barnstead, N.H.

[73] Assignee: Rochal Industries, Inc., Boca Raton, Fla.

[21] Appl. No.: 416,924

[22] Filed: Oct. 4, 1989

Related U.S. Application Data

[63] Continuation-in-part of Ser. No. 256,651, Oct. 12, 1988, abandoned.

[51] Int. Cl.$^5$ .................. A61L 13/00; A61F 13/00; A61F 15/00
[52] U.S. Cl. .................. 128/156; 128/DIG. 21; 604/304; 424/447; 525/477
[58] Field of Search .................. 128/156, DIG. 21; 604/304; 424/447; 523/111; 525/477

[56] References Cited

U.S. PATENT DOCUMENTS

| | | | |
|---|---|---|---|
| 3,577,516 | 5/1971 | Gould et al. | 128/155 |
| 3,987,000 | 10/1976 | Gleichenhagen et al. | 128/156 |
| 4,287,177 | 9/1981 | Nakashima et al. | 424/DIG. 13 |
| 4,291,025 | 9/1981 | Pellico | 128/156 |
| 4,303,066 | 12/1981 | D'Andrea | 128/156 |
| 4,318,746 | 3/1982 | Claffey et al. | 106/194 |
| 4,393,048 | 7/1983 | Mason, Jr. et al. | 424/132 |
| 4,569,784 | 2/1986 | Moore | 252/315.1 |
| 4,650,817 | 3/1987 | Allen, Jr. et al. | 523/105 |
| 4,838,253 | 6/1989 | Brassington et al. | 128/156 |

*Primary Examiner*—Randall L. Green
*Assistant Examiner*—Paul Prebilic
*Attorney, Agent, or Firm*—Wolf, Greenfield & Sacks

[57] ABSTRACT

Combinations of alky siloxy siloxane-containing polymers admixed with liquid polydimethylsiloxanes are excellent non-stinging, non-irritating liquid coating material for forming films which act as conformable bandages adhering to and protecting nails, skin and mucous membrane wounds from abrasion, contamination, and desiccation, while stopping pain from exposed nerve ends and allowing body fluid evaporation.

23 Claims, No Drawings

CONFORMABLE BANDAGE AND COATING MATERIAL

RELATED APPLICATION

This Application is a Continuation-in-Part of U.S. patent application No. 07,256,651, filed Oct. 12, 1988 now abandoned.

BACKGROUND OF THE INVENTION

The invention pertains to liquid adhesive materials which are useful for protecting surfaces such as biological surfaces, including skin and mucous membranes. The polymer component of the liquid adhesive material comprises an ethylenically unsaturated addition polymerizable monomer containing at least one alkyl siloxy silane. The polymer may also include other monomers.

The polymer, when incorporated into volatile liquid polydimethylsiloxanes, preferably with a small amount of polar liquids or solvents, provides for a fast drying, flexible, waterproof, breathable, non stinging liquid adhesive coating or bandage. This liquid adhesive coating may contain medicants or other active materials which may be gradually released onto targeted areas, if desired

PRIOR ART

Naturally occurring and derivatized naturally-occurring polymers have been tested as liquid adhesive coatings for bandage applications and, in some cases, utilized commercially. Typical examples are nitrocellulose in various solvents (e.g., New Skin-Medtech Laboratories, Inc., Cody, Wyo.), aqar in water and diethylene glycol (U.S. Pat. No. 4,291,025) carrageenan and hydroxypropylmethyl cellulose in water (U.S. Pat. No. 4,318,746), and alginate in glycerin (U.S. Pat. No. 4,393,048). All of these natural polymers can support microbial growth, hence requiring the addition of a preservative or antimicrobial agent to the product. The liquid bandages based on water, diethylene glycol, glycerin, etc. are not only susceptible to microbial growth, but are often also slow drying due to high heats of vaporization; and are often water sensitive, which can result in problems when used on areas of the body exposed to water. One commercial product, New Skin, does dry rapidly and is not water sensitive, but can cause stinging and further irritation of the skin upon application.

A few synthetic polymers have been patented for use as liquid adhesive coatings for bandage applications, most notably polymers containing 2-hydroxyethyl methacrylate (U.S. Pat. No. 4,303,066). These bandages based on the use of solvents can sting abraded areas; and the films can swell and wash off when in contact with water. U.S. Pat. No. 4,569,784 claims an ointment, not a long lasting bandage composed of an emulsion of water and silicone fluids, among other fluids. This reference can provide for an immediate soothing, but often not long lasting, treatment of the skin or mucous membranes. It also does not provide for fast drying, abrasion resistance, and other attributes which a polymer film can provide.

Additionally, traditional wound and surgical bandages, such as Band-Aids (Johnson & Johnson, New Brunswick, N.J.), comprised of film backings with adhesive, may contain silicones as part of either the adhesive or the backing (e.g. U.S. Pat. No. 4,650,817). These products are not applied as liquid adhesive coating where films form and adhere directly on the skin.

SUMMARY OF THE INVENTION

It is an object of the invention to provide a liquid polymer-containing coating material which can act as a bandage or dressing to protect wounds, when applied in liquid form and air dried on the wound to form an adherent, solid protective film without significant stinging to the skin or mucous membranes of the user.

It is a further object of the invention to provide a coating which will prevent further microorganism or particulate contamination to skin or mucous membrane wounds or incisions.

It is a further object of the invention to provide a non tacky, transparent covering which does not attract or hold dirt and can remain colorless and clear for wound viewing as well as cosmetic attractiveness.

It is a further object of the invention to provide a coating which, when applied, will control body fluid loss from an abraded area.

It is a further object of the invention to provide a polymer film in which medicants or other active agents, e.g. perfumes, may be incorporated for gradual release into targeted areas.

It is a further object of the invention to provide a coating which, when applied, repels liquid $H_2O$, but also allows $H_2O$ vapor to pass through.

It is a further object of the invention to provide a low surface tension covering which can reduce drag.

The liquid polymer containing coating materials of this invention consist essentially of a siloxane containing polymer and a solvent system comprising a polar solvent in small amount and a volatile liquid which is non-stinging to a user but provides bulk and formability to the liquid. Preferably the polymer is present from 1 to 40% by weight, the volatile liquid from 59.9 to 98.9% by weight and the polar solvent from 0.1 to 10% by weight. When the polar solvent is eliminated, the volatile liquid can be in amounts of 60 to 99%. The solvent is minimized to obtain flowability desired at the lowest solvent level feasable which minimizes stinging. The material forms a coating or bandage in the form of a dried film when applied to a surface or the skin of a user.

Preferably, the siloxane containing polymer comprises at least one vinyl-containing alkylsiloxysilane and an addition polymerizable comonomer. The volatile liquid is preferably a polydimethylsiloxane.

It is a feature of the invention that the liquid materials can act at room temperature (20° C.) when applied to skin, nails, or mucous membranes of a user to form films in minutes which films are excellent bandages. They are not a nutrient source for microorganisms, are conformable, comfortable and can be elastic and flexible. The films do not irritate the skin and mucous membrane when sprayed or deposited in any way during application and in use after drying. The bandages are substantially painless and can be easily removed substantially without pain. The dried bandages formed are substantially non water-sensitive, and waterproof and have high water vapor and oxygen gas transmission therethrough. The bandages form when applied over surfaces wet with water, blood or body fluids, in short times at standard room temperature and reasonable variants thereof. The liquid composition and/or dried polymer film can have various medicaments or other agents incorporated therein for maintaining sterility and/or for release to the underlying area of the body of a user. For example, perfumes, antibacterial or similar materials can be released from the coatings.

DESCRIPTION OF PREFERRED EMBODIMENTS

The siloxane-containing polymers of this invention can comprise vinyl containing alkylsiloxysilanes alone or as co-, ter or multi component polymers which can include other polymerizable monomers that do not make the polymers hydrophilic.

Typical vinylalkylsiloxysilanes that may be utilized are:
3-methacryloyloxy-propyltris(trimethylsiloxy)silane (TRIS);
3-methacryloyloxypropylpentamethyldisiloxane;
3 methacryloyloxypropylbis(trimethylsiloxy)methylsilane;
3-acryloyloxypropylmethylbis(trimethylsiloxy)silane;
3-acryloyloxypropyltris(trimethylsiloxy)silane; and others.

Typical addition polymerizable monomers which may be reacted with the vinylalkylsiloxysilanes to form multipolymers are: methyl methacrylate, methyl acrylate, tetrahydrofurfuryl methacrylate, cyclohexyl acrylate, tetrahydrofurfuryl acrylate, n-lauryl acrylate, n-lauryl methacrylate, 2-phenoxyethyl acrylate, 2-phenoxyethyl methacrylate, isodecyl acrylate, isodecyl methacrylate, isooctyl acrylate, isooctyl methacrylate, isobornyl acrylate, isobornyl methacrylate, benzyl methacrylate, 2-butoxyethyl acrylate, n-butyl acrylate, n-butyl methacrylate, ethyl acrylate, ethyl methacrylate, dimethyl itaconate, di-n-butyl itaconate, 2-ethylhexyl acrylate, 2-ethylhexyl methacrylate, furfuryl methacrylate, n-hexyl acrylate, n-hexyl methacrylate, isobutyl acrylate, isobutyl methacrylate, isopropyl methacrylate, methyl acrylate, alpha methyl styrene, styrene, p-t-butyl styrene, 4-methoxystyrene, n-octadecyl acrylate, n-octadecyl methacrylate, 2-phenylethyl methacrylate, n-tridecyl methacrylate, vinyl benzoate, vinyl naphthalene. In addition fluorinated siloxanes, fluorinated itaconates, fluorinated methacrylates or acrylates, such as hexafluoroisopropyl methacrylate, can be used.

Any hydrophobic polymerizable monomer can be used as long as the resulting copolymer has desired $O_2$ and $H_2O$ vapor permeability. These additional polymerizable comonomers can be present in amounts up to 0.85 mole fraction.

The polymers of the invention are preferably in proportions between about 15–100 mole% vinylalkylsiloxysilane which component maintains the desired compatibility of the polymer in the volatile liquid polydimethylsiloxanes with polar additives, provides high moisture and oxygen permeability, and provides biocompatibility. A range of 20 to 40 mole of the vinylalkylsiloxysilane in the polymer is preferred in the polymer of this invention. Other addition polymerizable monomers may be copolymerized with the vinylalkylsiloxysilanes between about 0–85% mole of the polymer composition to adjust permeability, adhesion, toughness, elasticity, temperature stability, and impact resistance, among other film qualities.

The polymers may be linear, branched, or slightly cross-linked and can be homo-, co-, ter- or multi-polymers. They may be random copolymers or segmental in nature.

Typical vinylalkylsiloxysilane monomers can have the following formulas:

$$CH_2=C(R^1)COOR^2SiR^3R^4R^5$$

Where $R^1 = H$, $CH_3$, or $CH_2COOR$,
Where $R^2 =$ alkyl $(C_1-C_4)$ or $CH_2CH(OH)CH_2$,
Where $R^3$, $R^4$, $R^5 = OSi(Y)_3$, or alkyl $(C_1-C_6)$,
Wherein, at least one of $R^3$, $R^4$, $R^5 = OSi(Y)_3$,
Where $Y =$ alkyl $(C_1-C_6)$ $OSi(Z)_3$ or $$R^2OOC(R^1)C=CH_2,$$

Where $Z =$ alkyl $(C_1-C_6)$, aryl, and
Where $R' = R^2SiR^3R^4R^5$. The polymers may have molecular weights from 50,000 to several million. The preferred molecular weight range is 50,000 to 500,000 weight average molecular weight. Lower molecular weight polymers have notably higher solubility in the solvents and solvent systems of this invention and hence, while they can be film formers, they generally are slow to dry and remain tacky. Higher molecular weight polymers are not soluble or dispersable in the solvents or solvent systems of this invention and therefore do not provide optimum film formation or flow properties. It is important for quick, non-tacky drying of the wound dressing that the polymer be in a poor solvent system. This is achieved by monomer choice, molecular weight control, and solvent system choice. The molecular weight of the polymers may be controlled by varing initiator, initiator concentration, reaction temperature, reaction solvent, and/or reaction method.

Any free radical initiator can be used in forming the polymers including azobisisobutyronitrile; 2,2'-azobis-(2,4-dimethylpentanenitrile); 2,2'-azobis- (2 methylbutanenitrile); potassium persulfate; ammonium persulfate; benzoyl peroxide; 2,5-dimethyl 2,5 bis (2-ethylhexanoylperoxy) hexane; and the like. The polymerization can be carried out by solution, emulsion, or suspension techniques.

The polymers of the invention are incorporated into a solvent system comprising volatile liquid silicones, preferably polydimethylsiloxane (preferably having a solubility parameter of 6.8–7.2 $(cal/cm^3)^{\frac{1}{2}}$) and if desired, a small amount (0.1–10 wt%) of polar liquid (preferably having a solubility parameter greater than or equal to 9 $(cal/cm^3)^{\frac{1}{2}}$) By utilizing a solvent system of this nature, the cast films dry more rapidly and are less sticky during drying. Moreover, the polar liquid or solvent can be used in minimized amount to minimize stinging. Volatile polydimethylsiloxanes (e.g. hexamethyl disiloxane, octamethyl cyclotetrasiloxane, decamethyl cyclopentasiloxane or octamethyl trisiloxanes and the like), are non-stinging, have a low heat of vaporization, are inert, and are non-irritating. The use of these liquids simply or in combination as the primary liquid phase of the liquid coating provides for comfort to a wounded area when used as a bandage, rather than further irritation and also allows for a higher oxygen and moisture vapor permeation rate while present.

The polar liquid or solvent when used preferably is a substance with a solubility parameter greater than or equal to 11.0 $(cal/cm^3)^{\frac{1}{2}}$, such as: ethanol, 95% ethanol-5% water, isopropanol, propanol, diethylene glycol, propylene glycol, ethylene glycol, N-methyl pyrrolidone or glycerol. Alcohols, esters, such as acetates, and organic acids, such as acetic acid, can also be used as the polar solvent. The polar liquids can function to further chain extend the polymer incorporated into the liquid polydimethylsiloxanes. The polydimethylsiloxanes are not true solvents for the polymers of the invention and the preferred polar liquids are solvents. The combination of the polydimethylsiloxanes and the polar solvents causes the polymers to chain extend and flow as liquids. In some cases, the polar liquid need not be used where solubility modification is not required. When polymers of the invention are of lower molecular weight in the range of 100,000 or lower, they generally can be incorporated into the polydimethylsiloxane solvent without the addition of adjunctive polar solvent. Also, if the polymers of the invention are not purified by precipitation, but rather distillation, when the reaction liquor is polydimethysiloxane, the polymers of the invention remain incorporated and do not require adjunctive polar solvent. Thus, the coating of this invention can be made without the use of polar liquids in some cases. The polymers can be synthesized in the organic liquid such as neat hexamethylene disiloxane, without precipitation or separation of the polymer phase. The unreacted monomers can then be distilled out of the reaction liquor, after polymerization is essentially complete, leaving the polymer dissolved in the reaction liquor to produce useful, non toxic coating compositions.

Polymer films of the invention cast from liquids containing good solvents with solubility parameters of between about 9 to 10 (cal/cm$^3$$^{\frac{1}{2}}$), (e.g. tetrahydrofuran and ethyl acetate) will function, but are generally slow to dry and remain tacky for extended periods.

Other substances may be added to the liquid material or formulation for plasticization, improved adhesion, or rheology control, and the like. Typical plasticizer/adhesion promoters are dibutylphthalate, acetyl tributyl citrate, sucrose acetate isobutyrate, sucrose benzoate, acetyltriethyl citrate, mineral oil, decamethyl cyclopentasiloxane, octamethyl cyclotetrasiloxane, butyl glycolate, and others.

Typical rheology additives that may be utilized are fumed silica, bentonite and other clay derivatives, and saturated fatty acids, such as hydrated ricinoleic acid.

The liquid adhesive material, composed of the polymer, solvent system, and additives, is useful for protecting or treating skin, nails and mucous membranes, e.g., skin cuts, abrasions, incisions and blisters; dry cracked skin; abraded gums and other oral surfaces; hemorrhoids and abraded body areas; inflammed digestive tract; and, other mucosal membrane incision and wounds.

As the liquid bandage is non-stinging and instantly covers exposed nerve endings, pain is stopped immediately. The bandage remains adherent to the skin/mucosal surface for 1-3 days, relieving pain and gradually lifting off without creating damage or further irritation.

Normal unabraded skin looses moisture vapor at an average rate of 200 g/m$^2$/day in most areas; the palms of the hand and soles of the feet respire at an average of 500 g/m$^2$/day. The liquid adhesive bandages of this invention have moisture vapor transmission rates of 200–700 g/m$^2$/day depending on protective polymer film thicknesses (0.0005–0.010 inches), thus preventing both dehydration of wounded areas and occlusion of body fluids. The polymers of this invention have exceptional oxygen permeability (DK) of about $120 \times 10^{-11}$ (cm$^2$/sec) (ml O$_2$/ml mm Hg) and the liquid adhesive coatings and bandages incorporating these polymers have oxygen permeability of about $80 \times 10^{-11}$ (cm$^2$/sec) (ml O$_2$/ml mm Hg) at 35° C.

The liquid adhesive coatings of this invention may be applied to the skin, mucous membranes, etc. in liquid form by utilization of a brush, rod, finger, sponge, cloth, dropper, etc; in spray or mist form; or any other usable technique for applying a liquid to a surface.

Medicants may be incorporated into the liquid or solid, dried film bandages for ready or continual release as the invention provides for an inert, longlasting, highly permeable film which can contain medicant or other active agents to be applied to the skin, mucous membranes, and other body areas on which it is desired to release the active agent over an extended period of time. Examples of useful medicants are fungicides, antibacterial agents, antiviral agents, antitumor agents, blood pressure and heart regulators, and many more. Other types of active agents which may be desirable to incorporate include perfumes, plant growth regulators, plant insecticles, UV and IR absorbers, etc.

The liquid adhesive coating of this intention could be used for application other than medical body care. For instance, the coating could be used as a water repellent, yet H$_2$O vapor permeable, film applied to sanitary napkins, diapers, or panties. With the incorporation of mildewcides, the liquid adhesive coating could be used to cover grout in tiled surfaces. The liquid adhesive is also useful as an insulative layer in the manufacture of electronic devices such as printed circuits, integrated circuits and interconnects. The liquid adhesive coating is further useful as a sunscreen with the incorporation of UV absorbers. Still other uses include forming films for use in eliminating chapped lips, treating skin and internal body surfaces, and providing protection to skin and other surfaces which may be medicated prior to application.

The following examples and test results are illustrative of the invention but are not meant to be limiting thereof.

EXAMPLE 1

A 500 resin kettle with overhead stirrer, N$_2$ inlet, condenser, and oil bath was set up in a hood. 14.25 g (0.034 mol) of 3-methacryloyloxypropyl(trimethylsiloxy) silane (TRIS) and 0.75 g (0.008 mol) of methyl methacrylate were dissolved in 150 g ethyl acetate. After charging this solution to the resin kettle and heating to 78° C., a solution of 1.5 g azobisisobutyronitrile (AIBN) in 10 g ethyl acetate was charged. The polymerization ran for 4 hours at 78° C. The low molecular weight product was precipitated into methanol, oven-dried and dissolved in hexamethyl disiloxane. When cast onto glass, the polymer in hexamethyl disilozxane produced an adherent, tacky film which can be used as a pressure sensitive adhesive for a variety of substrates such as glass, or can be used as an adhesive for a bandage of cloth or plastic substrate.

EXAMPLE 2

A 50 ml reaction flask was charged with 2.5 g ethyl acetate, 2.5 g (0.006 mol) (TRIS) and 0.09 g 2,5-dimethyl-2,5-bis(2-ethylhexanoylperoxy)hexane; flushed with nitrogen for 15 minutes, and completely closed to air. The polymerization was run for 94 hours at 65° C. The low molecular weight product when cast provided an elastic, waxy continuous film which was readily soluble in hexamethyl disiloxane.

EXAMPLE 3

To a 50 ml reaction flask was charged 19.76 g ethyl acetate, 4.28 g (0.010 mol) TRIS, 0.78 g (0.008 mol) methyl methacrylate, 0.29 g (0.002 mol) cyclohexyl methacrylate, and 0.003 g azobis(isobutyronitrile). The reaction mixture was flushed with nitrogen for 20 minutes and then stoppered. The polymerization was run at 60°-70° C. for approximately 10 days. A film cast from the mother liquor was non-tacky, elastic, and relatively tough. The dried polymer was marginally soluble in hexamethyl disiloxane.

EXAMPLE 4

To a 50 ml reaction flask was charged 20.16 g ethyl acetate, 2.5 g (0.006 mol) TRIS, 2.01 g (0.02 mol) methyl methacrylate, 0.25 g (0.001 mol) 2-ethylhexyl acrylate, and 0.003 g azbis(isobutyronitrile). The reaction mixure was flushed with nitrogen and then stoppered. The polymerization was run at 60°-70° C. for 4 days. A film cast from the mother liquor was clear, adherent, flexible and tough. The dried polymer was marginally soluble in hexamethyl disiloxane. A 0.016 in. thick film cast from the mother liquor had a moisture vapor transmission rate of 83 g/m$^2$/24 h; a 0.0045-0.005 in. thick film had a moisture transmission rate of 126 g/m$^2$/24h; and, a 0.0025-0.003 in. thick film had a moisture vapor transmission rate of 180 g/m$^2$/24h.

EXAMPLE 5

To a 50 ml reaction flask was charged 19.19 g ethyl acetate, 2.2g (0.005 mol) TRIS, 3.78 g (0.027 mol) n-butyl methacrylate, and 0.002 g azobisisobutyronitrile. After flushing with nitrogen, the flask was stoppered, the reaction run at 60°-70° C. for 6 days. The resultant polymer was precipitated into methanol and dried at 110° C. for 4 hours. The dried polymer was incorporated into hexamethyl disiloxane. A 0.025 in. thick film of the polymer cast from the mother liquor gave a moisture vapor transmission rate of 37.9 g/m$^2$/24h.

EXAMPLE 6

A 500 ml resin kettle, equipped as in Example 1, was charged with 27.40 g (0.065 mol) TRIS, 18.54 g (0.185 mol) methyl methacrylate, 4.10 g (0.022 mol) 2- ethylhexyl acrylate, and 194 g ethyl acetate. After heating to 48° C., 0.01 g of 2,2'-azobis (2,4-dimethylpentanenitrile) dissolved in 3.09 g ethyl acetate was added and the polymerization run for 16 hours. At which time, 0.01 g of 2,2'-azobis (2,4-dimethylpentanenitrile) dissolved in 3.09 g ethyl acetate was again added to the reaction continued to run for another 24 hours. The product was precipitated in methanol and air dried. The dried product was partially soluble in hexamethyl disiloxane.

EXAMPLE 7

Precipitated and dried polymer (1.02 g) from Example 6 was dissolved in 4.02 g ethyl acetate, when cast into a 0.004 in film, provided a moisture vapor rate of 126 g/m$^2$/42h.

EXAMPLE 8

Precipitated dried polymer (1.01 g) from Example 6 was dissolved in 5.40 g ethyl acetate with sucrose acetate isobutyrate (0.34g). This formulation provided an adherent, non tacky film with a moisture vapor transmission rate of 180 g/m$^2$/24h at a 0.0035 in. film thickness, and 613 g/m$^2$/24h at 0.0005-0.001 in. film thickness.

EXAMPLE 9

Precipitated dried polymer (1.05 g) from Example 6 was dissolved in 5.44 g ethyl acetate and 0.31 g decamethyl cyclopentasiloxane, and then cast into a 0.004 in. film provided a moisture vapor transmission rate of 180 g/m$^2$/24h.

EXAMPLE 10

Precipitated dried polymer (1.04 g) from Example 6 was dissolved in 6.76 g ethyl acetate and 0.65 g decamethyl cyclopentasiloxane, and when cast into a 0.0002 in film provided a moisture vapor transmission rate of 866 g/m$^2$/24h.

EXAMPLE 11

A 50 ml reaction flask was charged with 30 g ethyl acetate, 5 g (0.012 mol)TRIS, 0.8 g (0.004 mol) 2-ethylhexyl acrylate, 4.2 g (0.029 mol)n-butylmethacrylate, and 0.4 g of a 0.36% solution of 2,2'-azobis(2,4-dimethylpentanenitrile) in ethyl acetate. After nitrogen flushing for 20 minutes, the flask was stoppered and placed in a 40° C. oven for 5 days. After precipitation in methanol and air drying, the resultant polymer was soluble in hexamethyl disiloxane containing some methanol.

EXAMPLE 12

To a reaction, equipped as in Example 1, was charged 10.35 g (0.025 mol) TRIS, 3.87 g (0.039 mol) methyl methacrylate, 3.87 g (0.034 mol) ethyl methacrylate, 0.02 g 2,2'-azobis (2-methyl butanenitrile), and 42.0 g hexamethyldisiloxane (HMDS). The polymerization was run 6 hours at 80° C. and then terminated by the addition of air. The polymer was precipitated into cold methanol with a resultant 86% yield of polymer. Films (0.0014-0.0018 in. thick) cast from the mother liquor produced moisture vapor transmission rates of 630 g/m$^2$/24 h.

EXAMPLE 13

To a reaction, equipped as in Example 1, was charged 49.5 g (0.117 mol) TRIS, 20.0 g (0.2 mol) methyl methacrylate, 20.7 g (0.18 mol) ethyl methacrylate, 0.08 g 2,2'-azobis(2-methylbutanenitrile), 105.01 g 95% ethanol, and 105.03 g HMDS. The polymerization was run for 24 hours at reflux, 74° C. The polymer was then precipitated into water, washed repeatedly, and oven dried at 250° F. for 6 hours to produce an 86% yield. The resultant polymer had a M$_W$ of 164,200, M$_n$ of 114,600 and a polydispersity ratio of 1.43.

EXAMPLE 14

A 1000 ml resin kettle equipped as in Example 1 was charged with 210 g hexamethyl disiloxane, 210 g 95% ethanol, 99.21 g (0.235 mol) TRIS, 40.09 g (0.400 mol) methyl methacrylate, 40.09 g (0.351 mol) ethyl methacrylate, and 0.16 g 2,2'-azobis-(2-methylbutanenitrile) and the reaction ran at 75° C for 22 hours. The polymer was then precipitated into water and dried for 12 hours at 110° C. to give an 89% yield. When incorporated into 435 g hexamethyl disiloxane and 5.06 g 95% ethanol, the polymer (65.80 g) provided a cast film with an oxygen permeability of $120 \times 10^{-11}$ (cm$^2$/sec) (ml O$_2$/ml mm Hg) at 35° C.

EXAMPLE 15

The polymer (1.26 g) of Example 14 was incorporated into a liquid adhesive bandage composition composed of 0.10 g 95% ethanol, 0.15 g sucrose acetate isobutyrate, 8.22 g hexamethyl disiloxane, and 0.01 g Thixin R (NL Chemicals, Hightstown, N.J.). The resultant cast film, after two weeks of aging at room temperature, has an oxygen permeability of $80 \times 10^{-11}$ (cm$^2$/sec) (ml O$_2$/ml mm Hg) at 35° C.

EXAMPLE 16

The resultant dried polymer (2.34 g) from Example 14 was added to 15.30 g hexamethyl disiloxane, 0.36 g ethanol, and 0.18 g sucrose acetate isbutyrate. Films (0.002–0.003 in. thick) cast from this liquid coating formulation produced moisture vapor transport rates of $340 \pm 20$ q/m$^2$/24 h.

EXAMPLE 17

To 3.97 g of polymer prepared as in Example 14 were added 0.29 g 95% ethanol, 0.61 g octamethyl cyclotetrasiloxane, 0.29 g sucrose acetate isobutyrate, and 23.65 g hexamethyldisiloxane. The liquid adhesive bandage composition produced moisture vapor transport rates of 285 g/m$^2$/24 h from a 0.004 in film, 560 g/m$^2$/24 hr from a 0.001 in film, and 610 g/m$^2$/24 hr from a 0.0005 in film.

EXAMPLE 18

Liquid adhesive coating formulations prepared as in Example 17 were used on numerous occasions on minor cuts and abrasions by male and female human adults for the relief of pain. In each case, wound pain was relieved immediately upon application of the liquid bandage. The individuals had full use of the wounded areas without pain during healing.

EXAMPLE 19

An adult male accidentally cut off the tips of his right middle and index fingers excising at least the epidermis and the dermis; he applied the liquid bandage formulation as prepared in Example 17 and found immediate complete relief from pain. He reapplied the bandage once a day. During healing he had full use of his fingers without pain. The wound did not form a scab and healed without scarring.

EXAMPLE 20

An adult male accidentally sheared off the back of one of his teeth exposing the nerve. Upon application of the liquid bandage, as prepared in Example 17, he found immediate relief of pain. He applied the bandage once a day for two days until he could see a dentist for repair to the tooth. The bandage remained adherent to the tooth and surrounding gingival and periodontal tissue during utilization.

EXAMPLE 21

Two teenage males and one teenage female covered poison ivy inflammations with a liquid bandage, prepared as in Example 17 except in aerosol form, and found immediate complete relief from itching. They treated the poison ivy throughout its term and were not bothered by itching.

EXAMPLE 22

An adult male accidentally cut himself with a knife on his left index finger, upon applyinq liquid bandage prepared as in Example 17, the wound pain was relieved immediately. The wound healed in two to three days with no scab formation or scarring.

EXAMPLE 23

An adult male applied a liquid bandage, prepared as in Example 17 except in aerosol form, to hemorrhoids and obtained relief from the pain caused by the condition.

EXAMPLE 24

An adult male applied a liquid bandage, prepared as in Example 17 except in aerosol form, to mosquito bites and completely relieved all itching associated with these bites.

EXAMPLE 25

To 22.08 g of liquid bandage prepared as in Example 17 was added 0.41 g of isopropyl xanthic disulfide, a fungicide. The isopropyl xanthic disulfide was completely soluble in the liquid bandage formulation both in liquid form and when dried. The dried film was transparent yellow in color.

EXAMPLE 26

A 1000 ml. reaction kettle equipped with an overhead stirrer, N$_2$ purge, condenser, and heating mantle is charged with 70 g hexamethyl disiloxane, 16.5 g (0.039 mol.) TRIS, 13.2 g (0.132 mol.) methylmethacrylate, 0.30 g (0.002 mol.) iso-octyl acrylate, and 0.026 g 2,5-dimethyl-2,5 bis(2-ethylhexanoylperoxy)hexane is charged. After the reaction is terminated by the addition of air and lowering of temperature, the reaction liquor is added to water. The hexamethyldisiloxane is evaporated and the precipitated polymer dried at 105° C. for 12 hours to give a 64% yield. The resultant polymer (2.99 g) when incorporated into 11.96 g hexamethyldisiloxane and 0.40 g 95% ethyl alcohol produces a tough, elastic, adherent film.

EXAMPLE 27

The reaction of Example 26 is terminated after 18 hours at 74° C. by the addition of air. The temperature is then raised to 100° C. to allow distillation of the hexamethyldisiloxane containing unreacted methylmethacrylate and isooctylacrylate. The distillate is filtered through a charcoal containing column to trap unreacted monomers and circulated back to the reaction kettle. The resultant purified liquid product produces a tough, elastic, adherent film when cast.

In one preferred liquid polymer-containing material, methyl methacrylate is present in a mole fraction of from about 0.3 to 0.4, ethyl methacrylate is present in a mole fraction of about 0.3 to 0.4, and 3-methacryloyloxypropyltris(trimethylsiloxy) silane is present in a mole fraction of from about 0.2 to 0.4.

In still another liquid polymer-containing bandage material, from about 10 to 25% of a siloxane containing polymer is used along with about 0.5 to 5.0 wt% octamethyl cyclotetrasiloxane, about 0.5 to 5.0 wt% 95% ethanol-5% water, and about 65 to 89 wt% of hexamethyl disiloxane to form a liquid polymer-containing bandage material having a moisture vapor permeability of from 200 to 700 g/m²/24 hr and an oxygen permeability of 60 to 180×10⁻¹¹ (cm²/sec) (ml O₂ml mm Hg).

The above examples are representative of specific embodiments of the present invention. However, many variations are possible. In all forms, the liquid polymer containing coating material of this invention contains a siloxane-containing polymer and a solvent system comprising a major portion of a polydimethylsiloxane or mixture of such siloxanes and, if desired, a minor portion of a polar liquid or solvent or mixture thereof. In all cases the invention provides a method of forming a bandage on the body by applying a liquid polymer containing bandage formulation or material to the body and volatilizing the solvent system to form a bandage, which is adherent to the body while providing good moisture transmission properties and protecting the skin or body surface of the user.

What is claimed is:

1. A liquid polymer-containing bandage material comprising from 1 to 40 wt. % siloxane containing polymer, 59.9 to 98.9 wt. % volatile polydimethylsiloxane liquid, and 0.1 to 10 wt% polar liquid; said bandage material being substantially non stinging and film forming at room temperature to form an adherent comformable moisture vapor permeable bandage directly on a user.

2. A liquid polymer-containing bandage material in accordance with claim 1 wherein said siloxane containing polymer comprises at least one vinyl containing alkylsiloxysilane monomer being present in a mole fraction of 1.0 to about 0.15 and having the following structure:

$$CH_2=C(R^1)COOR^2SiR^3R^4R^5$$

Where $R^1$ = H, $CH_3$, or ,
Where $R^2$ = alkyl ($C_1$–$C_4$), aryl, or $CH_2CH(OH)CH_2$,
Where $R^3$, $R^4$, $R^5$ = $OSi(Y)_3$, or alkyl ($C_1$–$C_6$),
Wherein, at least one of $R^3$, $R^4$, $R^5$ = $OSi(Y)_3$
Where Y = alkyl ($C_1$–$C_6$) $OSi(Z)_3$ or

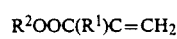

Where Z = alkyl ($C_1$–$C_6$), and
Where $R' = R^2SiR^3R^4R^5$.

3. A liquid polymer containing bandage material according to claim 2 wherein said siloxane-containing polymer comprises an addition polymerizable comonomer being present in a mole fraction of up to about 0.85 and is selected from the group consisting of methyl acrylate, methyl methacrylate, tetrahydrofurfuryl acrylate, tetrahydrofurfuryl methacrylate, cyclohexyl acrylate, cyclohexyl methacrylate, n-lauryl acrylate, n-lauryl methacrylate, 2-phenoxyethyl acrylate, 2-phenoxyethly methacrylate, 2-phenylethyl acrylate, 2-phenylethyl methacrylate, n-tridecyl acrylate, n tridecyl methacrylate, isodecyl acrylate, isodecyl methacrylate, isooctyl acrylate, isooctyl methacrylate, isobornyl acrylate, isobornyl methacrylate, benzyl acrylate, benzyl methacrylate, 2-butoxyethyl acrylate, 2-butoxyethyl methacrylate, n-butyl acrylate, n-butyl methacrylate, ethyl acrylate, ethyl methacrylate, 2-ethylhexyl acrylate, 2-ethylhexyl methacrylate, furfuryl acrylate. furfuryl methacrylate, n-hexyl acrylate, n-hexyl methacrylate, octadecyl acrylate, octadecyl methacrylate, isobutyl acrylate, isobutyl methacrylate, isopropyl acrylate, isopropyl methacrylate, d-methyl styrene, styrene, p-t-butyl styrene, 4-methoxystyrene, vinyl benzoate, vinyl naphthalene, hexafluoroisorpoyl methacrylate, fluorinated itaconates and admixtures thereof.

4. A liquid polymer-containing bandage material according to claim 2 wherein said vinyl-containing alkylsiloxysilane monomer is 3-methacryloyloxypropyltris(trimethylsiloxy)silane.

5. A liquid polymer-containing bandage material according to claim 3 wherein said addition polymerizable comonomer is a member selected from the group consisting of methyl methacrylate, ethyl methacrylate and admixtures thereof.

6. A liquid polymer containing bandage material according to claim 5 wherein 3-methacryloyloxypropyltris(trimethylsiloxy)silane is present in a mole fraction of about 0.2 to 0.4, methyl methacrylate is present in a mole fraction of about 0.3 to 0.4, and ethyl methacrylate is present in a mole fraction of about 0.3 to 0.4.

7. A liquid polymer-containing bandage material according to claim 1 wherein said volatile polydimethylsiloxane has a solubility parameter of about 7 (cal/cm³ⁱ) and is selected from the group consisting of hexamethyl disiloxane, octamethyl cyclotetrasiloxane, decamethyl cyclopentasiloxane, octamethyl trisiloxane and admixtures thereof.

8. A liquid polymer containing bandage material according to claim 7 wherein said volatile polydimethylsiloxane is a mixture of hexamethyl disiloxane and octamethyl cyclotetrasiloxane.

9. A liquid polymer containing bandage material according to claim 1 wherein said polar liquids have solubility parameters of greater than 9 (cal/cm³ⁱ).

10. A liquid polymer-containing bandage material according to claim 9 wherein said polar liquid has a solubility parameter of greater than or equal to 11.0 (cal/cm³ⁱ) and is selected from the group consisting of ethanol, 95% ethanol 5% water isopropanol, propanol, diethylene glycol, propylene glycol, triethylene glycol, N-methyl pyrrolidone, glycerol, and admixtures thereof.

11. A liquid polymer-containing bandage material according to claim 10 wherein said polar liquid is 95% ethanol.

12. A liquid polymer-containing bandage material according to claim 6 comprising of about 10 to 25 wt% said siloxane-containing polymer, about 0.5 to 5.0 wt% octamethyl cyclotetrasiloxane, about 0.5 to 5.0 wt% 95% ethanol 5% water, and about 65 to 89 wt% hexamethyl disiloxane; and having a moisture vapor permeability of from 200 to 700 g/m²/24 hr and an oxygen permeability of 60 to 180×10⁻¹¹ (cm²/sec) (ml O₂/ml mm Hg).

13. A liquid polymer-containing bandage material according to claim 1 comprising about 10 to 25 wt% said siloxane-containing polymer, about 0.5 to 5.0 wt% octamethyl cyclototrasiloxane, about 0.5 to 5.0 wt% 95% ethanol 5% water, about 0.5 to 5.0 wt% sucrose acetate isobutyrate, and about 60 to 88.5 wt% hexamethyl disiloxane; and having a moisture vapor permeability of from 200 to 700 g/m²24hr and an oxygen permeability of 60 to 180×10⁻¹¹ (cm²/sec) (ml O₂/ml mm Hg).

14. A liquid polymer-containing bandage material according to claim 1 which is formed into a dried film form.

15. A liquid polymer-containing bandage material according to claim 12 which is formed into a dried film form.

16. A liquid polymer-containing bandage material according to claim 13 which is formed into a dried film form.

17. A method of forming a conformable adherent bandage on the body of a user comprising.
   applying a liquid polymer-containing bandage material consisting essentially of a siloxane-containing polymer, a major amount of a volatile polydimethylsiloxane and a minor amount of a polar liquid to the body, and
   evaporating said polydimethylsiloxane and volatile liquid to form a conformable adherent bandage having good moisture vapor transmission properties, abrasion resistant properties and other necessary properties for use as a protective bandaging layer over the body.

18. A liquid polymer containing coating material comprising from 1 to 40 wt. % siloxane-containing polymer, 60 to 99 wt. % volatile polydimethylsiloxane, said coating material being substantially non-stinging, quick-drying and film forming at room temperature to form an adherent comformable moisture vapor permeable coating directly on a surface.

19. A liquid polymer-containing coating material in accordance with claim 18, and further comprising from about 0.1 to about 10% wt. % of a polar liquid.

20. A liquid polymer containing coating material in accordance with claim 18 in the form of a polymerized coating adherent to a body surface.

21. A liquid polymer-containing coating material in accordance with claim 20 in the form of a polymerized coating carrying an active agent therein for release to an underlying surface 22. A liquid polymer-containing coating material in accordance with claim 1 in the form of a polymerized coating adherent to a body surface.

23. A liquid polymer containing coating material in accordance with claim 22 in the form of a polymerized coating carrying an active agent therein for release to an underlying surface.

* * * * *